United States Patent [19]

Johnson, Jr.

[11] Plant 4,386

[45] Feb. 27, 1979

[54] STRAWBERRY PLANT

[75] Inventor: Harold A. Johnson, Jr., Watsonville, Calif.

[73] Assignee: Driscoll Strawberry Associates, Inc., Watsonville, Calif.

[21] Appl. No.: 886,697

[22] Filed: Mar. 15, 1978

[51] Int. Cl.[2] ..... A01H 5/03

[52] U.S. Cl. ..... Plt./48

[58] Field of Search ..... Plt./48-49

*Primary Examiner*—Robert E. Bagwill

[57] ABSTRACT

A strawberry variety chiefly characterized by its ability to produce large, showy berries from its crown crop early in March.

2 Drawing Figures

1

This invention relates to a new and distinct variety of strawberry plant known as H6 which is the result of a cross of the unpatented varieties known as the Driscoll Strawberry Associates' selections G7 and G8.

Seedlings resulting from the aforementioned cross were grown and asexually multiplied in Shasta County, California, and tested in the fruiting beds on the property of member growers of Driscoll Strawberry Associates, Inc. Clones of the seedlings were also held at the Propagation Nursery in Shasta County. One plant was selected from the aforementioned group of seedlings and further asexually reproduced in the Shasta County Nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising commercial variety.

Figure 1:
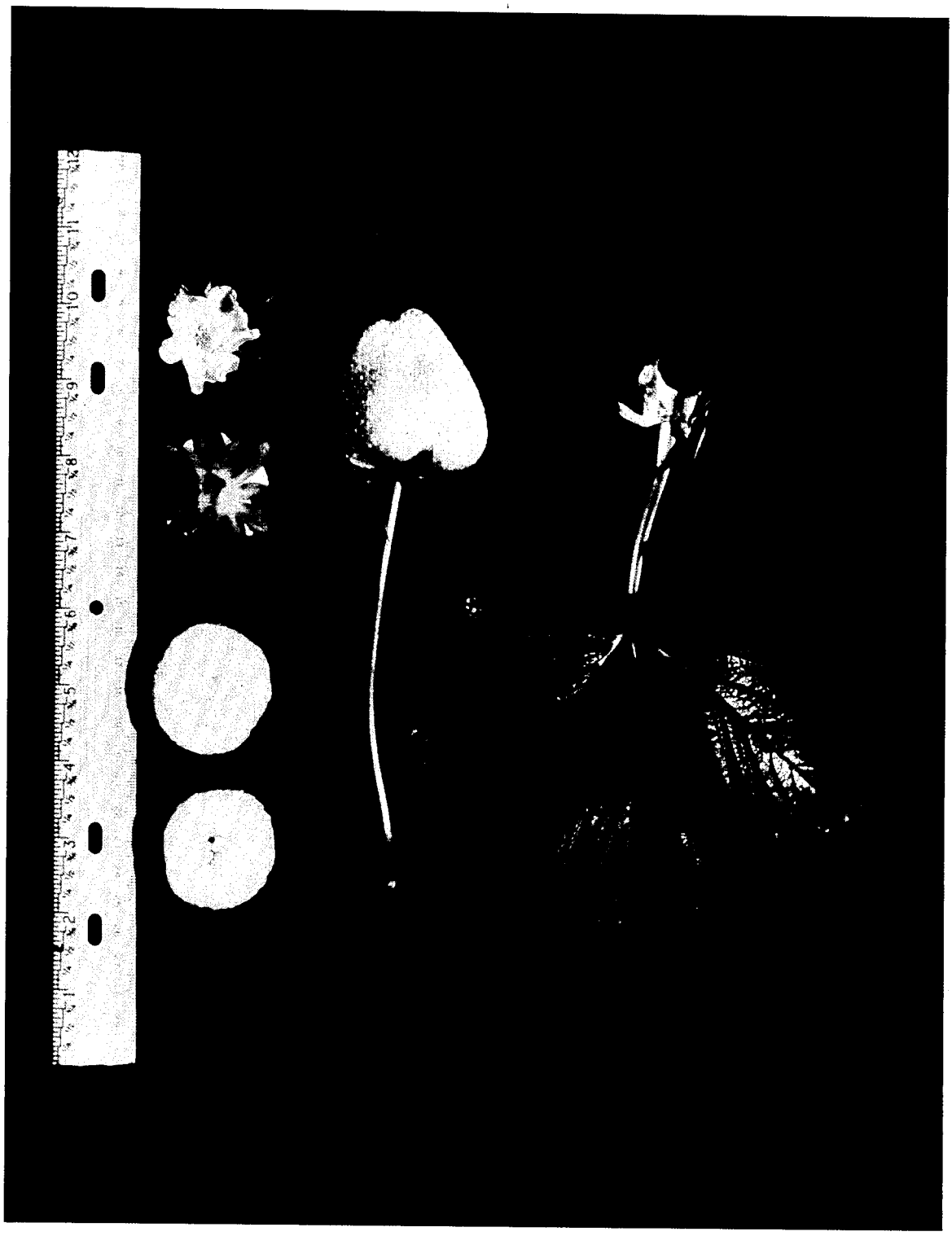

FIG. 1 of the accompanying drawings illustrates plant parts of the new variety, typical in size, shape and color.

Figure 2:
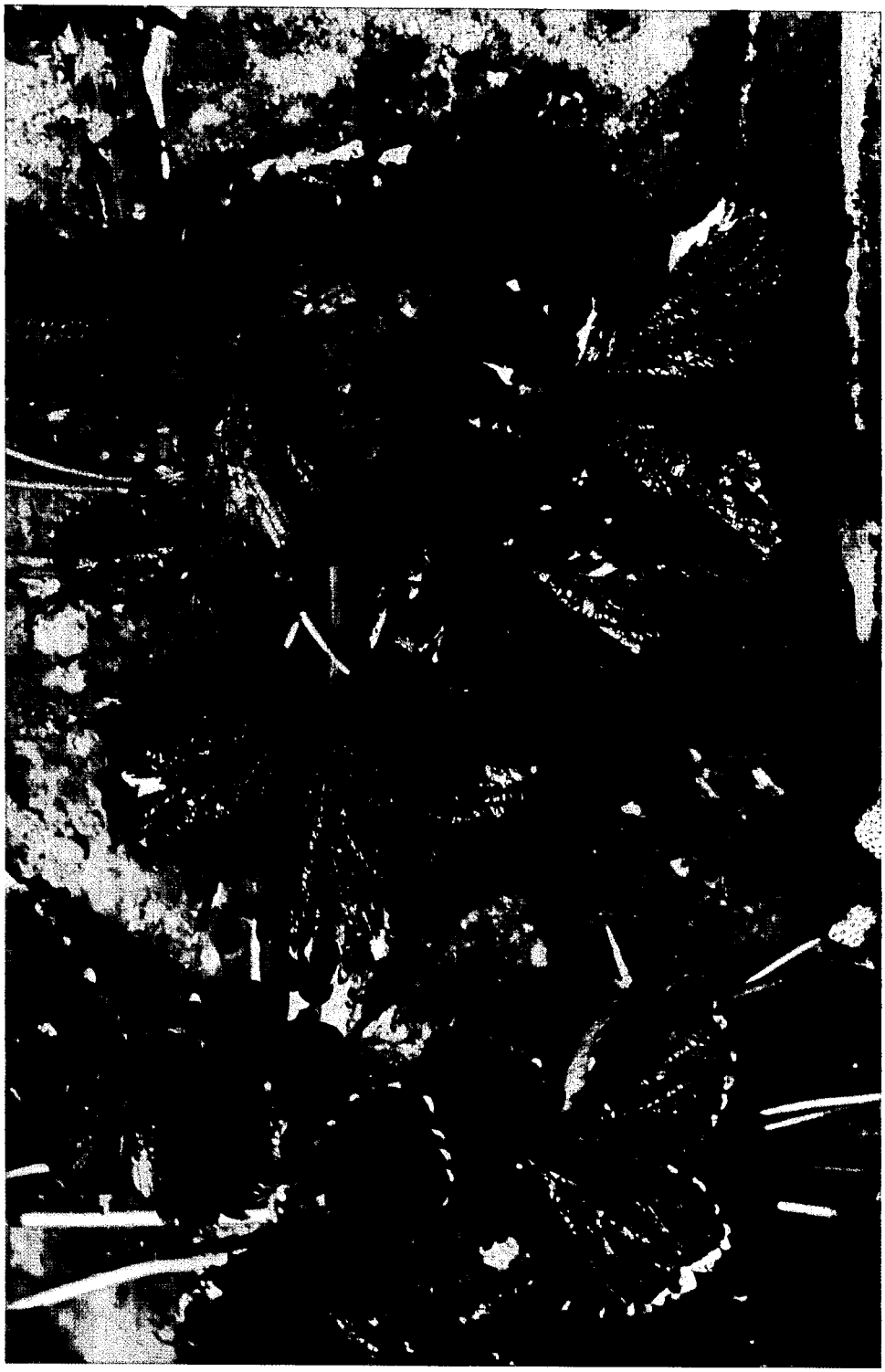

FIG. 2 of the accompanying drawings illustrates typical leaves of the new variety and shows the marginal burning of leaflets common in saline soils and a variegation of the leaflets common on a small percentage of plants.

A berry in cross section illustrates flesh color and characteristic core cavity of a berry that would be mature enough to be picked, but not totally ripe. The pedicel holding the near ripe berry is the extent of the inflorescence during the first crop that developes in Oxnard, Calif. during March. As the season progresses a more typical strawberry inflorescence developes with the pedicel holding the primary berry originating mainly from a peduncle, but with some pedicels originating from the axil formed by the peduncles. The pedicel also becomes longer as the season progresses. The berry shown is typical of the crown crop fruit during March, becoming conic to medium wedge in outline. The apex of long conic fruit often produce seed that is not fertilized as the stigma extends beyond the anthers so far that pollen has difficulty reaching the apex of the stigma unless bees are present and active. The anthers, however, produce an abundance of pollen. This gives the berry a light colored and often folded tip.

The surface is mainly smooth, with only a few longitudinal furrows appearing. The large calyx shown is also typical with some overlap and no serrations on the sepals. Some sepals, however, may have serrations present. The leaf shown, with its short petiole and leaflet

2 serrations are prone to become prematurely necrotic when the plant is being grown on saline soils.

The novel new winter planted spring variety is adapted mainly to use in Southern California. Its strongest character is its ability to produce large, showy berries from its crown crop early in March. This crop is similar to that of the fruiting pattern of TIOGA, the predominant winter planted variety being grown in Southern California when the data for this new variety was collected. TIOGA is a non-patented introduction of the University of California.

If nutritional requirements are provided without the presence of high salts, this new variety has the ability to continue to produce during the spring with a minimum of time between cropping peaks. The fruit size is larger than that of TIOGA, as well as having a smoother fruit surface and a more conic shape. The flavor is equal to TIOGA. The plant is smaller and lighter in color during most of the year. Individual petioles of the new variety are shorter especially early in the spring. The flower on the new variety is more visible than TIOGA, especially above the plant later in the spring. The TIOGA variety produces more fruit per inflorescence than the new variety. The TIOGA plant is also more tolerant to salt.

One of the distinguishing characteristics of the new variety as shown in FIG. 2, is the streak observed on a small percentage of its foliage when grown in the fruiting beds in spring (see drawing). This is a type of variegation that expresses itself differently than does BLAKEMORE or TRANSIENT YELLOWS, also a variegation, but a variegation that is detrimental to plant vigor. This streak type variegation also expresses itself in the fruit, giving some fruit light streaks visible on the fruit surface. Subsequent plant growth of individual plants showing streak tends to be free of this distinctive marker. The percentage of plants showing streak grown at the nursery is much less than that in the fruiting bed.

The crown crop is large and showy with good appearance, but the flesh and skin are not as firm as the Driscoll patented H4 (U.S. Plant Pat. No. 3,987) variety grown as a summer planted variety in Oxnard.

The aroma of the new variety is not distinctive. This variety has had limited exposure to the two-spotted mite, mildew and Mycosphaerella leaf spot, but appears to have moderate susceptibility to all of these pests. The leaflets are quite susceptible to injury from high levels of sodium and chlorides in the soil as the margins often become necrotic early in the fruiting season. As a seedling and selection, this new variety withstood the natural invasions of certain virus components found in Southern California without losing its ability to produce.

The varietal characteristics of the novel plant, described below in detail, were observed mainly during the early spring and June in Oxnard. The drawing was taken in Oxnard on March 29.

The color terminology as used herein is in accordance with Ridgway's Color Standards and Nomenclature (1912 Edition).

Plant: Medium size and vigor during early spring when free of high levels of salts which are often present in Southern California. Plant becomes large during late spring. It has an extensive root system.

Leaves: Leaflets are medium to large in size, central leaflet 7 to 9 cm. in length with the width less than the length. Petiole length is short, especially early in the fruiting season, 8 to 12 cm. early and 15 to 20 later. Bracts are often present on the petioles. The leaflet surface is mildy rugose and leaflets are mostly cupped upward. Immature leaflets are noticeably lighter in color than mature leaflets. Marginal burning of leaflets is common in saline soils. A variegation of the leaflets is common on a small percentage of plants. Color of upper side of mature leaflet during June is Cedar Green, Plate VI.

Runners: Runners are vigorous and abundant at the nursery, but not as abundant in the fruiting bed when the plant is given the correct amount of chilling for first year fruiting.

Inflorescence: A single pedicel coming from the crown is the only visible inflorescence during the early crown crop. Subsequent crops have a normal inflorescence with the pedicel holding the primary berry originating from both the axil formed by the union of peduncles and from the side of one of the peduncles. The hair on pedicels 20 cm. from tertiary fruit is perpendicular to the pedicel but hairs are not strong and may be erratic in the way they are held on the pedicel. Pollen is abundant but anthers are not held close enough to stigmas to give consistent fertilization when the flowers are large early in the year.

Fruit: Large, especially crown crop berries early in spring, 40 to 50 cm. in length with the width less than the length. Subsequent crops produce smaller fruit, especially after secondary and tertiary berries are initiated. Fruit shape is mostly conic to medium wedge as described in U.S.D.A. Bulletin 1043. Shoulders are strongly rounded, not necked. Some slight longitudinal furrows. Folded seedy tips are common giving a light colored apex, but the surface is mainly smooth. Seed are held slightly exerted or equal to the fruit surface. The skin and flesh are medium in firmness and rated good in flavor panels. The color of the fruit surface is Scarlet Red, Plate I, and the flesh is Scarlet, Plate I near the surface and Strawberry Pink, Plate I, near the core. The seed is yellow, but darkens when exposed to full sun.

Calyx: Large and showy, often 40 cm. in diameter on primary fruit. Individual sepals usually have a minimum of overlap and many have no serrations. The calyx is mostly clasping. Color of side of sepals facing fruit is Parrot Green, Plate VI.

I claim:

1. The new and distinct variety of strawberry plant herein described and illustrated, and identified by the characteristics enumerated above.

* * * * *